(12) United States Patent
Christian et al.

(10) Patent No.: US 8,900,513 B2
(45) Date of Patent: Dec. 2, 2014

(54) METHODS AND DEVICES FOR STERILIZING AND HOLDING BUFFERING SOLUTION CARTRIDGES

(71) Applicant: Onpharma, Inc., Los Gatos, CA (US)

(72) Inventors: Jeffrey J. Christian, Morgan Hill, CA (US); Harry Nguyen, Westminster, CA (US); Matthew J. Stepovich, Santa Cruz, CA (US)

(73) Assignee: Onpharma, Inc., Los Gatos, CA (US)

( * ) Notice: Subject to any disclaimer, the term of this patent is extended or adjusted under 35 U.S.C. 154(b) by 0 days.

(21) Appl. No.: 14/056,291

(22) Filed: Oct. 17, 2013

(65) Prior Publication Data

US 2014/0044594 A1 Feb. 13, 2014

Related U.S. Application Data

(60) Division of application No. 12/833,356, filed on Jul. 9, 2010, now Pat. No. 8,585,963, and a continuation-in-part of application No. 12/766,259, filed on Apr. 23, 2010.

(60) Provisional application No. 61/270,571, filed on Jul. 9, 2009, provisional application No. 61/276,137, filed on Sep. 8, 2009.

(51) Int. Cl.
*A61L 11/00* (2006.01)
*G01N 1/10* (2006.01)
*A61L 2/04* (2006.01)

(52) U.S. Cl.
CPC .............. *A61L 2/04* (2013.01); *A61L 2202/21* (2013.01)
USPC ................. 422/1; 422/50; 422/500; 436/180

(58) Field of Classification Search
CPC ............ B01L 1/00; A61L 2/00; A61L 2/0023
USPC .................................. 422/1, 50, 500; 436/180
See application file for complete search history.

(56) References Cited

U.S. PATENT DOCUMENTS

| | | | |
|---|---|---|---|
| 1,616,202 A | 2/1927 | Shook et al. | |
| 1,757,809 A | 5/1930 | Montuori | |
| 2,484,657 A | 10/1949 | Son | |
| 2,604,095 A | 7/1952 | Brody | |
| 3,737,608 A | 6/1973 | Nagao et al. | |
| 3,993,751 A | 11/1976 | Zinke | |
| 3,993,791 A | 11/1976 | Breed et al. | |

(Continued)

OTHER PUBLICATIONS

Difazio, et al. Comparison of pH-adjusted lidocaine solutions for epidural anesthesia. Anesth Analg. Jul. 1986;65(7):760-4.

(Continued)

*Primary Examiner* — Monzer R Chorbaji
(74) *Attorney, Agent, or Firm* — Wood, Herron & Evans, LLP

(57) ABSTRACT

Trays comprising a base have a plurality of axial slots adapted to receive buffer or other medical solution containers within the slots. A spring or other compression element at the bottom of the slot is configured to engage a plunger at the bottom of the solution container when present in the slot so that pressure is applied to the contents of the container in order to stabilize the contents while the containers are sterilized at an elevated temperature.

8 Claims, 3 Drawing Sheets

(56) References Cited

U.S. PATENT DOCUMENTS

| | | |
|---|---|---|
| 4,154,820 A | 5/1979 | Simoons |
| 4,259,956 A | 4/1981 | Ogle |
| 4,513,015 A | 4/1985 | Clough |
| 4,630,727 A | 12/1986 | Feriani et al. |
| 4,654,204 A | 3/1987 | Copenhafer et al. |
| 4,704,088 A | 11/1987 | Newman |
| 4,753,345 A | 6/1988 | Goodsir et al. |
| 4,756,838 A | 7/1988 | Veltman |
| 4,795,441 A | 1/1989 | Bhatt |
| 4,959,175 A | 9/1990 | Yatzidis |
| 5,062,832 A | 11/1991 | Seghi |
| 5,137,528 A | 8/1992 | Crose |
| 5,149,320 A | 9/1992 | Dhaliwal et al. |
| 5,211,643 A | 5/1993 | Reinhardt et al. |
| 5,226,901 A | 7/1993 | Dhaliwal et al. |
| 5,261,903 A | 11/1993 | Dhaliwal et al. |
| 5,296,242 A | 3/1994 | Zander |
| 5,298,023 A | 3/1994 | Haber et al. |
| 5,318,544 A | 6/1994 | Drypen et al. |
| 5,320,804 A * | 6/1994 | Zakaria et al. .................. 422/21 |
| 5,330,426 A | 7/1994 | Kriesel et al. |
| 5,383,324 A | 1/1995 | Segers et al. |
| 5,439,643 A | 8/1995 | Liebert |
| 5,542,934 A | 8/1996 | Silver |
| 5,603,695 A | 2/1997 | Erickson |
| 5,609,572 A | 3/1997 | Lang |
| 5,609,838 A | 3/1997 | Neuman et al. |
| 5,610,170 A | 3/1997 | Inoue et al. |
| 5,690,215 A | 11/1997 | Kimball et al. |
| 5,779,357 A | 7/1998 | Jonsson et al. |
| 5,840,252 A | 11/1998 | Giertych |
| 5,984,906 A | 11/1999 | Bonnichsen et al. |
| 6,022,337 A | 2/2000 | Herbst et al. |
| 6,232,128 B1 | 5/2001 | Iguchi et al. |
| 6,432,089 B1 | 8/2002 | Kakimi et al. |
| 6,620,138 B1 | 9/2003 | Marrgi et al. |
| 6,692,468 B1 | 2/2004 | Waldenburg |
| 6,818,179 B1 | 11/2004 | Edgson et al. |
| 6,948,522 B2 | 9/2005 | Newbrough et al. |
| 7,445,801 B2 | 11/2008 | Faict et al. |
| 7,462,164 B2 | 12/2008 | Moir |
| 7,507,579 B2 | 3/2009 | Boccazzi et al. |
| 8,585,963 B2 | 11/2013 | Christian et al. |
| 2003/0015423 A1 | 1/2003 | LaGreca et al. |
| 2004/0175437 A1 | 9/2004 | Beckett |
| 2007/0265593 A1 | 11/2007 | Kitagawa et al. |
| 2007/0293441 A1 | 12/2007 | Choo et al. |
| 2008/0045925 A1 | 2/2008 | Stepovich et al. |
| 2009/0221984 A1 | 9/2009 | Girgis et al. |
| 2009/0292271 A1 | 11/2009 | Stepovich et al. |
| 2011/0165017 A1 | 7/2011 | Christian et al. |

OTHER PUBLICATIONS

Fitton, et al. The use of pH adjusted lignocaine in controlling operative pain in the day surgery unit: a prospective, randomised trial. Br J Plast Surg. Sep. 1996;49(6):404-8.

International search report and written opinion dated Sep. 8, 2010 for PCT Application No. US2010/041601.

Masters, et al. Randomised control trial of pH buffered lignocaine with adrenaline in outpatient operations. Br J Plast Surg. Jul. 1998;51(5):385-7.

McGlone, et al. Reducing the pain of intradermal lignocaine injection by pH buffering. Arch Emerg Med. Jun. 1990;7(2):65-8.

Metzinger, et al. Local anesthesia in blepharoplasty: a new look? South Med J. Feb. 1994;87(2):225-7.

Michaels. Sterilisation of sodium bicarbonate solutions. Pharm J. Sep. 4, 1948;107(4427):160-161.

Momsen, et al. [Neutralization of lidocaine-adrenaline. A simple method for less painful application of local anesthesia]. Ugeskr Laeger. Aug. 14, 2000;162(33):4391-4. (Article in Danish—English abstract only).

Nelson. Neutralizing pH of lidocaine reduces pain during Norplant system insertion procedure. Contraception. May 1995;51(5):299-301.

Office action dated Mar. 25, 2013 for U.S. Appl. No. 12/833,356.

Office action dated Oct. 19, 2012 for U.S. Appl. No. 12/833,356.

Palmon, et al. The effect of needle gauge and lidocaine pH on pain during intradermal injection. Anesth Analg. Feb. 1998;86(2):379-81.

Peterfreund, et al. pH adjustment of local anesthetic solutions with sodium bicarbonate: laboratory evaluation of alkalinization and precipitation. Reg Anesth. Nov.-Dec. 1989;14(6):265-70.

Ridenour, et al. Anesthetic efficacy of a combination of hyaluronidase and lidocaine with epinephrine in inferior alveolar nerve blocks. Anesth Prog. 2001 Winter;48(1):9-15.

Samdal, et al. Alkalisation of lignocaine-adrenaline reduces the amount of pain.during subcutaneous injection of local anaesthetic. Scand J Plast Reconstr Surg Hand Surg. Mar. 1994;28(1):33-7.

Sapin, et al. Reduction in injection pain using buffered lidocaine as a local anesthetic.before cardiac catheterization. Cathet Cardiovasc Diagn. Jun. 1991;23(2):100-2.

Schwab, et al. Bicarbonate buffering of local anesthetics. Am J Emerg Med. May 1996;14(3):339.

* cited by examiner

METHODS AND DEVICES FOR STERILIZING AND HOLDING BUFFERING SOLUTION CARTRIDGES

CROSS-REFERENCES TO RELATED APPLICATIONS

This application is a divisional of U.S. patent application Ser. No. 12/833,356 (now U.S. Pat. No. 8,585,963), filed Jul. 9, 2010, which claims the benefit of the following prior provisional application Nos. 61/270,571, filed on Jul. 9, 2009; 61/270,572, filed on Jul. 9, 2009; and 61/276,137, filed on Sep. 8, 2009, the full disclosures of which are incorporated herein by reference; U.S. patent application Ser. No. 12/833,356 (now U.S. Pat. No. 8,585,963), filed Jul. 9, 2010, is also a continuation-in-part of co pending application Ser. No. 12/766,259, filed on Apr. 23, 2010, the full disclosure of which is incorporated herein by reference.

BACKGROUND OF THE INVENTION

1. Field of the Invention

The present invention relates generally to methods and apparatus for sterilizing medical buffers and other solutions. More specifically, the present invention relates to methods and devices for holding medical buffers and solutions under pressure while undergoing heat sterilization.

A buffer solution is a solution that tends to change the pH of other solutions with which it comes in contact to the buffer solution's pH. Medical buffer solutions frequently contain bicarbonate ions and are used in numerous medical applications including antidotes, dialysates, body replacement fluids, body irrigating solutions, cardiac perfusates, and for many other purposes. One of the most commonly used medical bicarbonate buffer solutions consists of sodium bicarbonate ($NaHCO_3$) mixed with water, which among other things, can be used to buffer parenteral injections to a more physiologic pH prior to injection. Of particular interest to the present application, bicarbonate solutions may be used to buffer acidic local anesthetic injections in order to enhance anesthetic effectiveness, reduce injection pain, and limit tissue trauma. For use of sodium bicarbonate for buffering local anesthetic, as well as for other medical uses including but not limited to treatment of acidosis, it is desirable that sodium bicarbonate solutions be precisely maintained at or near a particular known pH. Using a buffer solution having a known pH allows a medical practitioner to mix a predetermined ratio of the buffer solution with the parenteral solution in order to achieve control over the resulting pH of parenteral solution, which has significant benefits over using a parenteral solution where the pH is not controlled.

As an example, when compounding 8.4% sodium bicarbonate buffer solution with commercially available cartridges of 2% lidocaine with epinephrine 1:100,000, the pH of the buffer solution will tend to drive the pH of the combination, almost exclusively of the pH of the commercially available anesthetic cartridges, such that a relatively small volume of buffer solution will have a disproportionately large impact on the pH of the combined solution. Thus, to achieve a parenteral solution with a predictable pH, it is important that the pH of the buffer solution be precisely known and controlled, in addition to knowing and controlling the amount of buffering solution to add to the local anesthetic. Only when the pH of the buffer solution being added and the amount of buffer being added are both known can the practitioner know and control the resulting pH of the buffered anesthetic.

Commercially produced sodium bicarbonate buffers do not provide buffer packages with precisely controlled pH. For example, an assay of the commercially available sodium bicarbonate solutions performed by the inventors showed a pH range from 7.62 to 8.26 in a number of commercially obtained bicarbonate buffer cartridges. Presumably the actual range of the product available in the marketplace is even wider than the range identified in this small assay.

It must be appreciated, in this context, that a medical buffer having an actual pH of 7.6 may perform significantly differently than a medical buffer having an actual pH of 8.3. This is true whether the medical buffer is designed to buffer the pH of the body's fluids, for instance in the treatment of acidosis, or the medical buffer is designed to buffer the pH of a parenteral solution prior to its use. In the example where a practitioner uses sodium bicarbonate solution to buffer anesthetic to achieve physiologic pH, the ratio of buffer solution to anesthetic solution will be quite different when the pH of the bicarbonate solution is 7.6 compared to when the pH is 8.3. Thus, prior art methods of combining buffering solution with parenteral solutions which rely on adding the same ratio of buffering solution to the parenteral solution, regardless of the actual pH of the buffer, will not consistently arrive at a desired pH for the buffered parenteral.

A method and system for adjusting the pH of medical buffers and other medical solutions to a precisely controlled value in a plurality of identical buffer cartridges or other containers is described in co pending application Ser. No. 12/766,259, filed on Apr. 23, 2010, the full disclosure of which is incorporated herein by reference. That application teaches that the pH of the solutions in individual containers can be adjusted by exposing those containers, while open, to an environment having a controlled temperature, humidity, pressure, and level of carbon dioxide. After the pH has equilibrated to a target pH, the cartridges can be sealed with no head space remaining within the cartridges. Once the cartridges are sealed, an inventory of cartridges having precisely controlled and identical pH values can be created. The need to sterilize the containers and their contents, however, can adversely affect the contents of the cartridges. Sterilization is typically done at elevated temperatures which can cause the buffer or other medical solution to boil, which can cause the seals to fail or can otherwise adversely impact the solution and the container.

For these reasons, it would be desirable to provide methods and apparatus for sterilizing cartridges and similarly packaged buffer solutions so as to prevent boiling and other adverse changes that might occur during heat sterilization. It would be particularly desirable to be able to sterilize multiple buffer or other medical solution packages simultaneously while holding the packages in trays or other containers that are also suitable for subsequent storage and shipment of the buffers. At least some of these objectives will be met by the inventions described hereinbelow.

2. Description of the Background Art

Glass vials and cartridges for storing medical solutions are described in U.S. Pat. Nos. 1,757,809; 2,484,657; 4,259,956; 5,062,832; 5,137,528; 5,149,320; 5,226,901; 5,330,426; and 6,022,337. Injection pens which employ drug cartridges are described in U.S. Pat. No. 5,984,906. Exemplary disposable drug cartridge that could be loaded with buffer solution in accordance with the present invention are described in U.S. Pat. No. 5,603,695 and in commonly owned, co pending application US2009/0292271 (U.S. Ser. No. 12/406,670), both of which are incorporated herein by reference. A device for delivering a buffering agent into an anesthetic cartridge using a transfer needle is described in U.S. Pat. No. 5,603, 695. Devices for maintaining a dissolved gas in solution in a pouch are described in U.S. Pat. Nos. 5,690,215; 5,610,170; and 4,513,015, and U.S. Patent Publ. No. 2007/0265593. Other patents and applications of interest include U.S. Pat. Nos. 2,604,095; 3,993,791; 4,154,820; 4,630,727; 4,654,204; 4,756,838; 4,959,175; 5,296,242; 5,383,324; 5,603,695; 5,609,838; 5,779,357; and U.S. Patent Publ. No. 2004/0175437. Literature publications describing buffering anesthetics with widely different ratios of a sodium bicarbonate solutions include Ridenauer et al., Anesth Prog, vol. 48, p. 9-15 (2000); Palmon et al., Anesth Analg, vol. 86, pp. 379-81 (1998); Metzinger et al., Southern Med J, vol. 87, no. 2 (1994); Nelson, Contracept, vol. 55, p. 299 (1995); Samdal, Scand J Plast and Recons Surg and Hand Surg, vol. 28, p. 33-37 (1993); Master, Br. J Plast Surg, vol. 51, p. 385 (1998); Difazio et al. Anesth Analg, vol. 65, p. 760 (1986); Fitton et al., Br. J Plast Surg, vol. 49, pp. 404-08 (1996); Peterfreund et al., Region Anesth, vol. 14, no. 6, p. 265 (1989); Momsen et al., Ugeskr Laeger, vol. 162, no. 33, p. 4391 (2000); Schwab et al. Am J Emerg Med, vol. no. 3 (1996); McGlone et al. Arch Emerg Med, vol. 7, pp. 65-68 (1990); and Sapin P, et al. Catheterization and Cardio Diag, vol. 23, pp. 100-102 (1991).

BRIEF SUMMARY OF THE INVENTION

The present invention provides methods and apparatus for sterilizing, transporting, and storing medical solution containers, such as cartridges and carpules, which hold injectable medical solutions, such as buffer solutions. Buffers and other medical solutions are often labile and at risk of boiling at the elevated temperatures used in sterilization. In particular, sodium bicarbonate buffer solutions are subject to the evolution out of solution of carbon dioxide ($CO_2$), which can affect the pH of the buffer if all of the liberated $CO_2$ does not return to solution upon cooling. While the following disclosure is directed particularly at methods and apparatus for sterilizing sodium bicarbonate buffers and other medical solutions having salts with a reversible equilibrium at near saturation, the invention extends to any medical solution held in a container or carpule which is subject to boiling or partial vaporization when sterilized in the cartridge at elevated temperatures.

The present invention is particularly intended for sterilizing and storing small medical cartridges, sometimes referred to as carpules, comprising a small glass or plastic vial having a needle-penetrable septum at a top end and a displaceable plunger at a bottom end thereof. Such cartridges can be placed in a syringe or other delivery system where a needle penetrates the septum to access the buffer or other contents and a shaft of the system advances the plunger to deliver the solution through the needle. A dosing pen system useful for buffering anesthetic cartridges with buffers prepared by the present invention is described in co pending application Ser. No. 12/406,670, filed on Mar. 18, 2009, the full disclosure of which is incorporated herein by reference.

Medical bicarbonate buffer solutions are buffers that rely on the combination of carbon dioxide ($CO_2$) with water to form carbonic acid ($H_2CO_3$) which dissociates to a hydrogen ion ($H^+$) and a bicarbonate ion ($HCO_3^-$). In using such bicarbonate solutions to buffer medical solutions, including local anesthetics such as lidocaine, articaine, prilocaine, and mepivacaine, both the amount of the bicarbonate solution and the pH of the bicarbonate solution used and the pH of the bicarbonate solution used are determinative of the pH of the medical solutions after the two solutions have been combined. Viewed differently, the amount of buffering solution needed to stabilize a medical solution at a particular target pH will depend on the pH of the buffering solution itself. Thus, a measured volume of buffering solution cannot be relied on to adjust the pH of a medical solution toward a target pH when the actual pH of the buffering solution varies significantly from its nominal pH, which would cause the stabilized pH of the buffered medical solution to differ significantly from the target value. Thus, any uncertainty or change in the pH of the buffering solution resulting from sterilization of the cartridge of buffering solution can significantly affect the pH of the anesthetic when combined with the buffer, making it very difficult for the physician to precisely control the buffered pH of the anesthetic delivered to a patient.

The present invention provides methods and apparatus which can stabilize the pH of the buffer or other medical solution sealed in a cartridge during heat sterilization. In particular, the present invention provides methods and holding or storage trays which can apply external pressure (above atmospheric pressure) to the medical solution within the container in order to raise the pressure of the solution to a level sufficient to inhibit or prevent boiling during the sterilization. While in some cases where boiling of the bicarbonate solution is prevented, some bubbles of carbon dioxide may temporarily initiate or form, the present invention will prevent irreversible carbon dioxide bubble formation, or formation of bubbles that do not return to solution during cooling of the solution after head sterilization. By applying the pressure and preventing the irreversible bubble formation, it has been found that deleterious changes in the pH of the medical solution can be prevented.

Surprisingly, the inventors have further discovered that applying a pressure which is too high (above an upper threshold or limit) can result in irreversible crystallization of salts in the buffer or other medical solution, which can make the solution unusable. In the case of the exemplary sodium bicarbonate buffers of the present invention, pressures applied above an upper threshold has been found to cause the buffer salt to crystallize in an irreversible manner, thus becoming a precipitate that makes the solution unsuitable for buffering parenteral solutions, and for many other medical purposes.

In a first aspect of the present invention, sealed containers filled with medical solutions are heat sterilized in a manner where a force is applied to the solution in the container, for instance by placing a force against a rubber stopper or plunge in a cartridge filled with the medical solution. The container is exposed to an elevated temperature sufficient to sterilize the container and the medical solution. The force applied to the stopper is sufficient to create pressure in the solution that inhibits boiling the water contained in the medical solution, as well as being sufficient to inhibit the evolution of vapors other than water out of solution (for instance carbon dioxide gas). By "sufficient to inhibit the evolution of vapors other than water out of solution," it is meant that the pressure will prevent the irreversible formation of such vapor bubbles within the solution while the solution is being held at the elevated sterilization temperature. In some cases, small vapor bubbles may transiently be produced, but such vapor bubbles will quickly disappear upon cooling, and the generation of such small vapor bubbles will not adversely affect the pH or other desirable characteristic of the medical solution. The external pressure that prevents this vapor formation must not be so high as to prevent thermal expansion of the fluid, which could cause the container or its seals to fail. Also significantly, the external pressure must be kept below an upper limit at which, if the pressure of the solution exceeds the limit, crystallization of the buffer or other species in the medical solution can occur.

The methods are particularly useful for sterilizing medical buffers, more particularly for sterilizing sodium bicarbonate buffers. For such bicarbonate buffers, the sterilization temperature is usually in the range from 100° C. to 140° C. and the internal pressure before, during, and after heat sterilization will being in the range from 0.7 kPa (14.7 psig) to 8.3 kPa (175 psig). The containers that are held under pressure in this range are usually exposed to the elevated temperature of a heat sterilizer for a duration that ranges from 3 minutes to 60 minutes, where longer times generally are used at lower sterilization temperatures.

In specific embodiments, the containers being sterilized will be cartridges that have an open interior filled with the medical solution, a needle-penetrable septum, and a plunger. The pressure on the solution may be applied by engaging a compression member, such as a coil or other spring, against the plunger. In some embodiments, the containers are held in a tray having a plurality of springs or other compression members arranged to engage the plungers to apply the pressure when said containers are placed in the tray. Usually, the tray includes a plurality of slots with the springs at one end of the slot. A retainer is typically used to hold a top of the container within the slot in order to push or compress the plunger within the container with a desired force (depending on the spring constant, degree to which the spring has been compressed, and the area of the plunger) sufficient to achieve the desired elevated pressure prior to and after the steam sterilization process. During the sterilization process itself, the characteristics of the spring must be such that the spring can absorb the thermal expansion of the fluid without which absorption, the container may shatter. Significantly, the spring must also be soft enough to absorb the thermal expansion of the solution and prevent the expansion In a second aspect of the present invention, a tray comprises a base having a plurality of aligned slots. Each slot is arranged to receive a container which holds a medical solution, such as a buffer. The compression member, such as a spring, is disposed at the bottom of each slot and is oriented to engage a plunger on a bottom of the medical solution container when the container is held within the slot. Retainers are disposed at the top of each slot and positioned to engage a top of the container to position the container axially within the slot so that the plunger on the container is held against the compression member at the bottom of the slot with a force (determined by the degree of compression of the spring or other compression member) sufficient to raise the pressure of the medical solution to a level which inhibits the evolution of vapor within the solution when the container is exposed to an elevated temperature sufficient to sterilize the solution.

The trays will typically be used to sterilize the containers as well as to ship and to store the containers. Thus, the present invention further comprises the trays having a plurality of containers therein, where the containers each contain a medical solution which has been sterilized while held within the tray. Typically, the medical solutions in each of the containers will be identical with identical characteristics. For example, the containers may each contain a sodium bicarbonate buffer having at or near identical pH and other characteristics within each of the containers.

When the tray is intended to hold containers with medical buffers, particularly sodium bicarbonate buffers, the compression member will be configured to raise the pressure to at least 0.7 kPa (14.7 psig) when the container is held within the slot, typically raising the pressure to a value in the range from 0.7 kPa to 8.3 kPa (175 psig) during heat sterilization. In the exemplary embodiments, the compression members are axially compressible springs, typically coil springs, with a spring constant in the range from 1.1 Nm to 11 Nm, and wherein the retainer is positioned to compress the spring by a distance in the range from 0.5 mm to 5 mm when the plunger has an area of 20 mm$^2$.

DETAILED DESCRIPTION OF THE INVENTION

Figure 1:
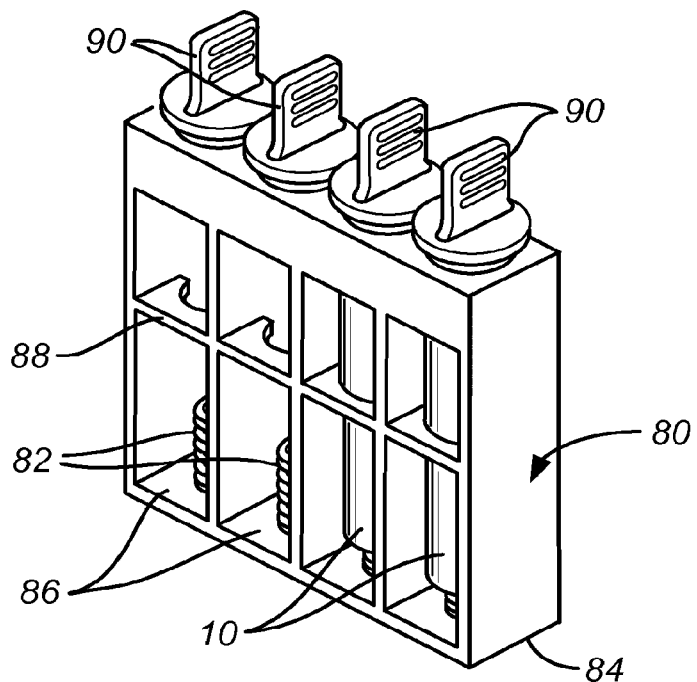
FIG. 1 is a perspective view of a sterilization and storage tray constructed in accordance with the principles of the present invention.
Figure 2:
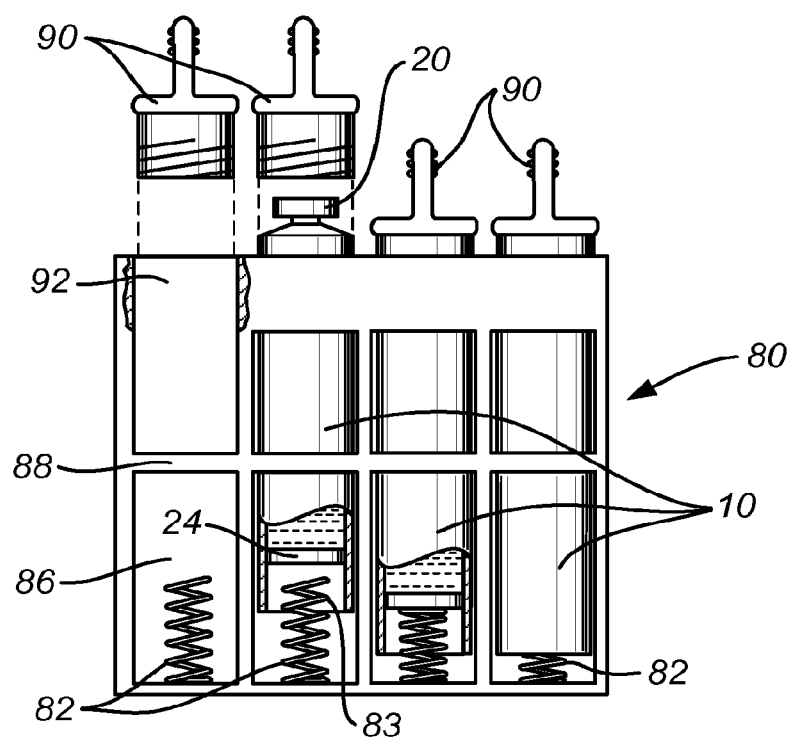
FIG. 2 is a front view of the storage and sterilization tray of FIG. 1 shown with one container removed, one container partially inserted into a slot, and two containers fully inserted into their slots.

Referring to FIGS. 1 and 2, a storage and sterilization tray 80 constructed in accordance with the principles of the present invention comprises a base 84 defining a plurality of axial slots 86, where each slot has a compression member, such as coil spring 82 at a bottom end and a removable retainer 90 at an upper end. The retainers 90 are removably received in openings 92 at the top of each axial slot, as best seen in FIG. 2. Single containers 10 are received in each slot 86 by passing the container downwardly through the opening 92 so that a movable plunger 24 at the bottom of the container engages the spring 82, as seen in FIG. 2. In particular, the cartridge 10 is inserted into the axial slot 86 so that the plunger 24 first engages a top 83 of the spring and then partially compresses the spring as shown in the two middle slots of the tray 80. Once the cartridge 10 is fully inserted, the retainer 90 can be replaced in the opening 92 to properly maintain the position of the cartridge so that the spring remains compressed to apply the desired compression force against the contents of the cartridge 24, as shown in the two right-hand slots of tray 80 in FIG. 2. The spring will not be fully compressed, thereby allowing thermal expansion to occur during heat sterilization such that the thermal expansion does not create sufficient pressure to either burst the container or cause crystallization of components of the solution.

Figure 3:
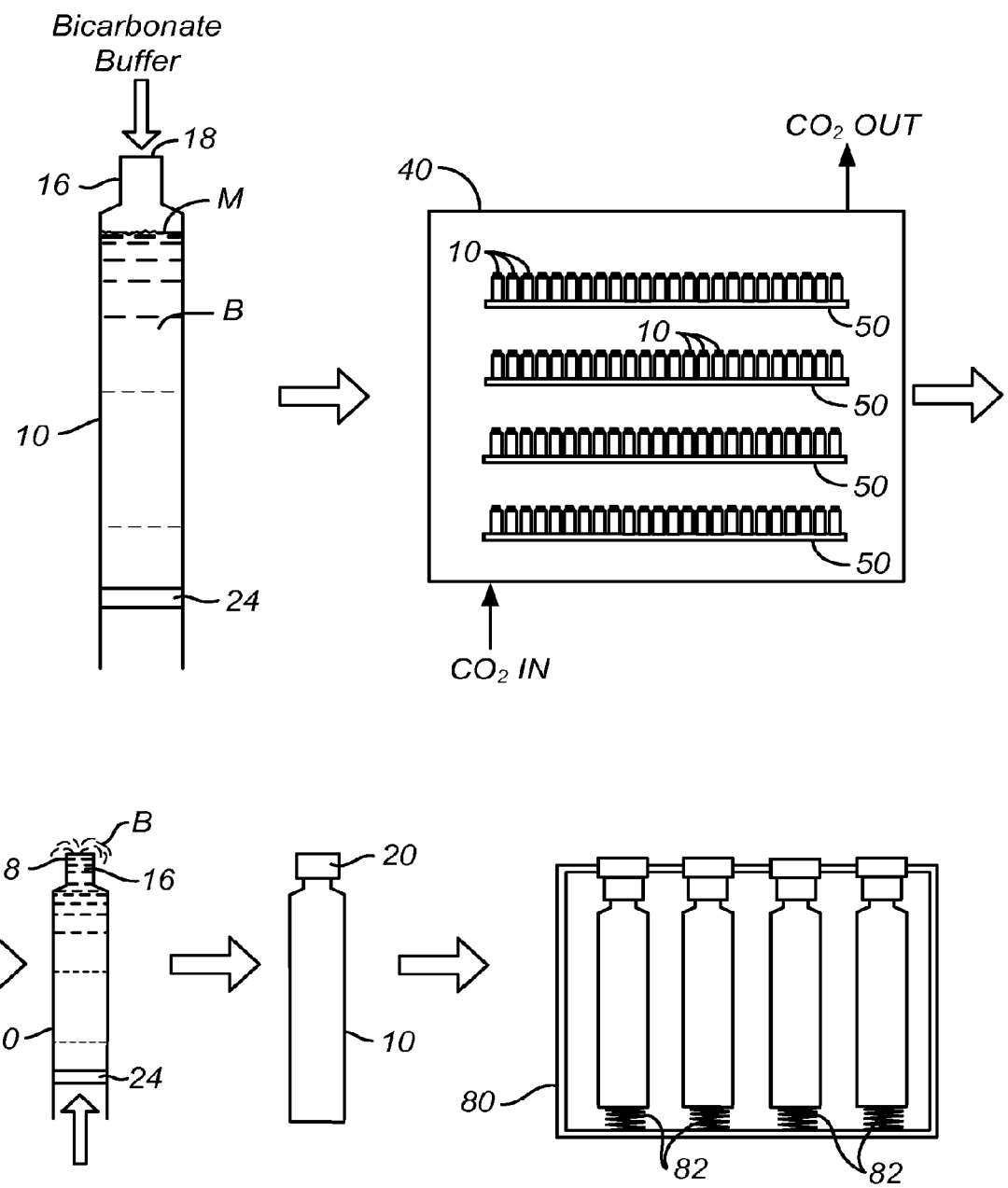
FIG. 3 illustrates a method for preparing pH-stabilized buffer cartridges by placing uncapped cartridges in a carrier that is placed in an pH equilibration chamber.

Referring now to FIG. 3, the trays 80 are particularly useful for sterilizing buffer cartridges 10 which have been filled with bicarbonate buffer which is then stabilized to an accurate and repeatable pH, as described in greater detail in co pending application Ser. No. 12/766,259, the full disclosure of which has been previously incorporated herein by reference. Initially, the individual buffer containers 10 are filled with the aqueous bicarbonate buffer B to appoint near meniscus M. Usually, the volume of buffer B introduced will be selected so that the upper surface or meniscus M of the buffer lies below the reduced diameter neck 16 so that the meniscus M has a larger area than it would have if it were present within the neck. This larger area allows the carbonic acid within the buffer to reach equilibrium with the carbon dioxide in the atmosphere within the chamber 40 more rapidly than if the area were reduced. The containers 10 are then introduced to the treatment chamber 40, typically after placement on carriers. After the containers 10 have been loaded onto the supports 50, they are left to equilibrate with the carbon dioxide environment which is continuously being replenished with the carbon dioxide gas for a number of hours under the conditions described above. After a sufficient time has passed for the buffer within the containers to equilibrate with the carbon dioxide within the treatment chamber 40, the containers are removed and the plungers 24 advanced to raise the level of buffer to the opening 18 in the neck 16. Caps 20 are then placed over the necks 16, leaving little or no head space, and the individual sealed containers 10 then placed in a storage tray 80 where springs 82 can be engaged against the plungers 24 to pressurize the buffers to inhibit the evolution of carbon dioxide gas from the buffer solution. By limiting such evolution, the pH of the buffer will be more stably maintained. The treatment trays 80 are also suitable for autoclaving the containers to assure sterility as described below. The containers may then be stored and distributed within the trays 80 or may be stored and distributed in separate containers.

Figure 4:
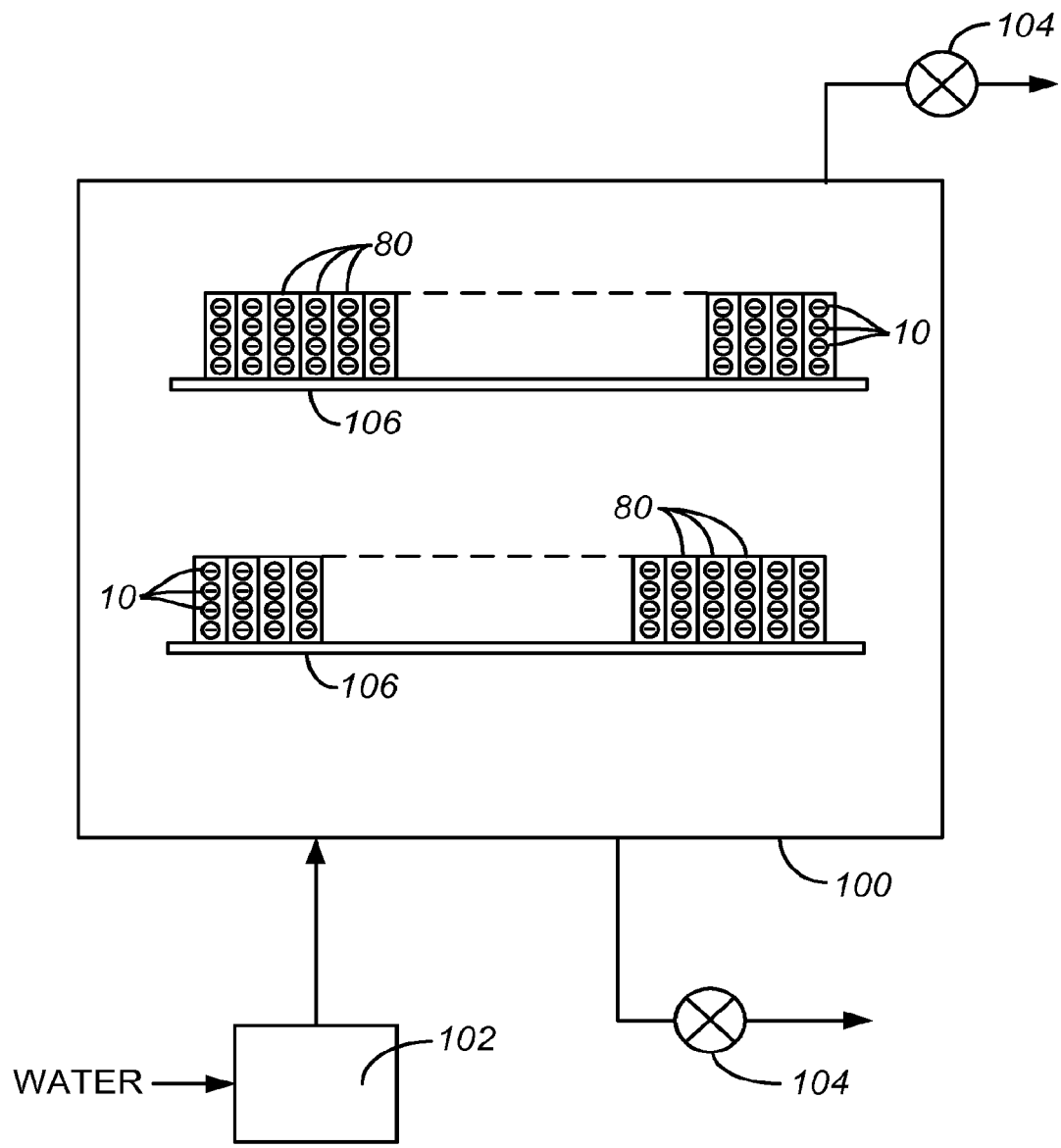
FIG. 4 illustrates a plurality of storage and sterilization trays being sterilized in an autoclave in accordance with the principles of the present invention.

Referring to FIG. 4, sterilization can be performed in an autoclave 100 which is designed to expose the trays 80 and the cartridges 10 therein to superheated steam at a temperature in the range from 100° C. to 150° C. The autoclave typically takes water, passes the water through a heater 102 which releases steam into the chamber of the autoclave 100. Steam and/or condensed water can be removed through upper or lower valves 104 to maintain the desired pressure, if any, and temperature within the autoclave 100. Suitable autoclaves are available from many commercial suppliers, such as the AMSCO Eagle Model 3000 SL Sterilizer, commercially available from Steris Corp., Mentor, Ohio 44060. The trays 80 are usually stacked on shelves 106 within the autoclave 100 and are held at the elevated temperature and pressure for sterilization times as described previously in this application. At all times, the springs 82 will be applying an elevated pressure, again within the ranges set forth above, to the buffer or other medical solutions within the containers in order to inhibit vaporization but allow for thermal expansion without creating crystallization. After the treatment time, the steam to the autoclave will be turned off and the temperature will return to ambient. When the trays 80 are removed from the autoclave 100, the buffer or other medical solution within the individual containers 10 will have been pH stabilized. Usually, the cartridges 10 may be maintained for storage, shipment, and inventory within the trays 80, further reducing the risk of damage or degradation to the containers or the medical solution contents.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for sterilizing a container filled with a medical solution comprising a buffer, which solution evolves vapor when heated, said method comprising:
   providing a sealed container having an open interior filled with the medical solution, a needle-penetrable septum, and a plunger;
   applying a pressure above atmospheric pressure to the medical solution within the sealed container by engaging a compression member against the plunger; and
   exposing the container to an elevated temperature sufficient to sterilize the medical solution within the container,
   wherein said temperature is sufficient to evolve the vapor at atmospheric pressure, and the applied pressure is sufficient to inhibit the evolution of the vapor within the container without precipitating the buffer.

2. A method as in claim 1, wherein the applied pressure allows for thermal expansion of the solution during sterilization, such that the solution does not achieve a pressure sufficient to cause the transformation of components of the solution to solid form.

3. A method as in claim 1, wherein the buffer is sodium bicarbonate, the sterilization temperature is in the range from 100° C. to 150° C., and the pressure applied to the solution before, during, and after autoclaving is at least 0.7 kPa (14.7 psig) but not more than 8.3 kPa (175 psig).

4. A method as in claim 3, wherein the container is exposed to the elevated temperature and the applied pressure for a time in the range from 3 minutes to 60 minutes.

5. A method as in claim 1, wherein a plurality of containers are held in a tray having a plurality of compression members arranged to engage the plungers to apply said pressure.

6. A method as in claim 5, wherein the applied pressure allows for thermal expansion of the solution during sterilization, such that the solution does not achieve a pressure sufficient to cause the transformation of the components of the solution to solid form.

7. A method as in claim 2, wherein the buffer is sodium bicarbonate, the sterilization temperature is in the range from 100° C. to 150° C., and the pressure applied to the solution before, during, and after autoclaving is a least 0.7 kPa (14.7 psig) but not more than 8.3 kPa (175 psig).

8. A method as in claim 7, wherein the container is exposed to the elevated temperature and the applied pressure for a time in the range from 3 minutes to 60 minutes.

* * * * *

UNITED STATES PATENT AND TRADEMARK OFFICE
CERTIFICATE OF CORRECTION

| | | |
|---|---|---|
| PATENT NO. | : 8,900,513 B2 | Page 1 of 1 |
| APPLICATION NO. | : 14/056291 | |
| DATED | : December 2, 2014 | |
| INVENTOR(S) | : Jeffrey J. Christian et al. | |

It is certified that error appears in the above-identified patent and that said Letters Patent is hereby corrected as shown below:

In the Specification:

At column 2, line number 28, change "is" to --are-- and at line number 61 change "cartridge" to --cartridges--

At column 3, line number 10, change "solutions" to --solution--

At column 4, line number 34, change "pressures" to --pressure-- and at line number 42 change "plunge" to --plunger--

At column 5, line number 4, change "being" to --be--

At column 6, line number 51, change "co pending" to --co-pending--

Signed and Sealed this
Thirty-first Day of March, 2015

Michelle K. Lee
*Director of the United States Patent and Trademark Office*